United States Patent [19]

Vangermain et al.

[11] 4,310,442

[45] Jan. 12, 1982

[54] SUPPORTED SILVER CATALYSTS MIXED WITH PROMOTER METAL COMPOUNDS FOR THE PRODUCTION OF ETHYLENE OXIDE

[75] Inventors: Erwin Vangermain; Claus-Dieter Mengler; Rainer Elm; Horst Ueberschaer; Wilhelm Brauckmann, all of Marl, Fed. Rep. of Germany

[73] Assignee: Chemische Werke Hüls AG, Marl, Fed. Rep. of Germany

[21] Appl. No.: 162,649

[22] Filed: Jun. 24, 1980

[30] Foreign Application Priority Data

Jun. 26, 1979 [DE] Fed. Rep. of Germany ....... 2925625

[51] Int. Cl.$^3$ ........................ B01J 21/12; B01J 23/50
[52] U.S. Cl. ................. 252/455 R; 252/475; 252/476
[58] Field of Search ........... 252/454, 475, 476, 455 R; 260/348.34, 348.35

[56] References Cited

U.S. PATENT DOCUMENTS

| | | | |
|---|---|---|---|
| 2,799,687 | 7/1957 | Gould et al. | 252/476 X |
| 3,420,784 | 1/1969 | Keith et al. | 252/454 X |
| 3,962,136 | 6/1976 | Nielsen et al. | 252/454 |
| 4,012,425 | 3/1977 | Nielson et al. | 260/348.34 |
| 4,039,561 | 8/1977 | Mitsuhata | 252/476 X |
| 4,066,575 | 1/1978 | Winnick | 252/476 |

*Primary Examiner*—Carl F. Dees
*Attorney, Agent, or Firm*—Wells & Wells

[57] ABSTRACT

The activity and the service life of supported silver catalysts used in the preparation of ethylene oxide by the catalytic vapor phase oxidation of ethylene with molecular oxygen are extended by using mixtures of:

(a) supported silver catalysts and promoter metal compounds;
(b) supported silver catalysts and supported promoter metal compounds;
(c) promoter metal compound treated supported silver catalysts and promoter metal compounds; or
(d) promoter metal compound treated supported silver catalysts and supported promoter metal compounds.

Promoter metal compounds containing about 0.001–0.05% by weight rubidium, about 0.01–0.20% by weight potassium, about 0.001–0.5% by weight cesium or about 0.01–0.25% by weight barium, based on the total weight of catalyst, are suitable.

8 Claims, No Drawings

SUPPORTED SILVER CATALYSTS MIXED WITH PROMOTER METAL COMPOUNDS FOR THE PRODUCTION OF ETHYLENE OXIDE

CROSS REFERENCES TO RELATED APPLICATIONS

Applicants claim priority under 35 USC 119 for application No. P 29 25 625.5-41, filed June 26, 1979 in the Patent Office of the Federal Republic of Germany.

The applications of Erwin Vangermain et al, entitled "Silver Catalysts for the Production of Ethylene Oxide", filed Mar. 31, 1980 and having Ser. No. 135,927; and entitled "Process for Activating or Reactivating Ethylene Oxide Silver Substrate Catalysts", filed Mar. 31, 1980 and having Ser. No. 136,045, are incorporated herein to show the preparation of silver catalysts for use in the production of ethylene oxide and to show an ethylene oxide process and apparatus wherein the present catalysts are useful, respectively.

BACKGROUND OF THE INVENTION

The field of the invention is improved silver catalysts for the production of ethylene oxide, their preparation and their use in ethylene oxide processes.

The state of the art of processes for preparing ethylene oxide by the catalytic vapor phase oxidation of ethylene with molecular oxygen in the presence of supported silver catalysts may be ascertained by reference to U.S. Pat. Nos. 4,012,425 and 4,039,561, the disclosures of which are incorporated herein. U.S. Pat. Nos. 3,793,231; 3,962,136 and 4,066,575 disclose the state of the art of silver catalysts for the production of ethylene oxide, the disclosures of which are incorporated herein. The reactivation of silver catalysts is disclosed in U.S. Pat. Nos. 4,051,068 and 4,125,480, the disclosures of which are incorporated herein.

U.S. Pat. No. 4,012,425 discloses a process for the production of ethylene oxide wherein ethylene is contacted in vapor phase with an oxygen-containing gas at ethylene oxide forming conditions at an elevated temperature of from 210° to about 285° C. in the presence of a fixed bed of a silver metal-containing catalyst. The catalyst is prepared by (a) impregnating a porous refractory catalyst support with a solution comprising solvent, silver salt sufficient to deposit from 2% by weight to 20% by weight of silver on the support and salts of one or more higher alkali metals in which the salts consist of salts of cesium or rubidium or mixtures thereof sufficient to deposit an amount of alkali metal in excess of $8.0 \times 10^{-3}$ gew per kilogram of total catalyst on the support;

(b) separating the impregnated support;

(c) reducing the silver salt present on the impregnated support to silver metal at a temperature of from about 100° to about 500° C.;

(d) contacting the impregnated support wherein silver is present as silver metal one or more times with an alkanol of 1 or 2 carbon atoms to selectively remove an amount of higher alkali metal present on the impregnated support such that the impregnated support so contacted contains $4.0 \times 10^{-5}$ to $8.0 \times 10^{-3}$ gew of higher alkali metal per kilogram of catalyst present in final form on the support in the form of an oxide in which the oxide consists of oxides of cesium or rubidium or mixtures thereof;

and (e) separating the impregnated support from the alkanol contacting solution and drying to substantially remove the residual alkanol present in and on the impregnated support.

Supported silver catalysts are used to prepare ethylene oxide by oxidizing ethylene with oxygen or oxygenated gases. It is also known to react these silver catalysts with so-called promoters, the earth-alkali-metal compounds. Barium compounds and/or alkali-metal compounds, especially those of the so-called heavy alkali-metals, rubidium and/or cesium are used as the promoters as disclosed in U.S. Pat. Nos. 3,962,136; 4,066,575 and 4,039,561. Ordinarily, the promoter metal compounds are deposited simultaneously with the silver during the preparation of the catalyst. The promoter metal compounds may also be deposited on the carrier after the silver has been deposited.

It is further known that silver catalysts lose selectivity in the course of time and that after several years' use the catalysts must be replaced by new catalysts. Exchanging catalysts which are degraded in performance by new ones is time consuming and labor intensive in large scale industrial plants. Furthermore, the changeover requires a production stoppage and high costs.

It is also known to improve the performance of a silver catalyst, i.e., to reactivate a used catalyst as disclosed in U.S. Pat. Nos. 4,051,068 and 4,125,480.

This reactivation is implemented for instance in large scale industrial plants by flooding the reactor filled with the catalyst with a solution of the promoter metal compound. After the excess solvent is removed, the residual solvent is eliminated by heating the catalytic bed and blowing an inert gas therethrough. This procedure requires the use of solvents and again causes a production stoppage.

SUMMARY OF THE INVENTION

Having in mind the limitations of the prior art, it is an object of the present invention to improve the performance of supported silver catalyst. Another object of the present invention is to sustain the use of the supported silver catalysts as long as possible. Still another object of the present invention is to postpone the time needed to exchange supported silver catalysts for new ones.

These objects are achieved according to the present invention by preparing physical mixtures of supported silver catalysts and promoter metal compounds. The promoter metal compounds may be used:

(a) directly where the external structures (shape and particle size) are suitable; or (b) as supported promoter metal compounds.

It is therefore possible to mix the supported silver catalyst with salts of the promoter metals when these salts are suitable as regards the structure of their crystals, shape and particle size. The support used for the promoter metal compounds appropriately are of the same shape and particle size as the supported silver catalyst so that a more uniform mixing is obtained. However, this is not required. The support for the promoter metal compounds may consist of the same base material as the silver support catalyst. However, other support materials may also be used provided they offer sufficient mechanical stability and are inert with respect to both the initial materials and the reaction products of the oxidizing process. Suitable supports are, for instance, pumice, porcelain, stoneware, alpha-aluminum oxide and Stuttgarter Masse (a silicate containing slight amounts of the oxides of sodium, iron, calcium and magnesium) but the present invention is not limited to these supports.

The amount of promoter metal contained in the overall mixture is within the conventional limits, namely between about 0.001 and 0.05% by weight of rubidium, 0.01 and 0.20% by weight of potassium, 0.001 and 0.5% by weight of cesium and 0.01 and 0.25% by weight of barium, referred to the total catalyst weight. By total catalyst weight is meant silver+support+promoter metal+support for promoter metal.

The proportion by volume of the support material containing the promoter metals may be varied within wide limits. In other words, even relatively large amounts of the promoter metals may be deposited on the supports, or pure promoter metal compounds of suitable external structure may be used. The proportion by volume of the support containing the promoter should not exceed 50% of the total mixture because otherwise the silver proportion for a given total volume would be too small. Advantageously, the proportion by volume will be between about 0.5 to 25%, especially between 5 and 15%. When the proportion by volume is too low (less than about 0.1%) there is inadequate distribution through the overall material.

Advantageously those compounds of the promoter metals are used which are volatile under the conditions of reaction.

Suitable promoter metal compounds are particularly barium compounds such as barium oxide, barium peroxide, barium hydroxide, barium nitrite, barium nitrate, barium carbonate, barium acetate, barium oxalate, barium tartrate, barium naphthenate, barium stearate, barium dodecanate, and chloride of barium and/or alkali metal compounds of rubidium and/or cesium such as rubidium oxide, rubidium peroxide, rubidium hydroxide, rubidium nitrite, rubidium nitrate, rubidium carbonate, rubidium acetate, rubidium oxalate, rubidium tartrate, rubidium stearate, rubidium dodecanate, rubidium chloride, cesium oxide, cesium peroxide, cesium hydroxide, cesium nitrite, cesium nitrate, cesium carbonate, cesium acetate, cesium oxalate, cesium tartrate, cesium stearate, cesium dodecanate and cesium chloride.

The procedure is applicable both to silver catalysts which already contain promoters and to those catalysts which do not contain them. In both cases the performance of the catalysts is enhanced and maintained over a longer time span.

The particle sizes of the supported silver catalysts (A), promoter metal compound treated supported silver catalysts (B), promoter metal compounds (C) and supported promoter metal compounds (D) are 2-10, especially 2-5 mm. They may be used in the form of spheres, rings, pellets or such bodies causing minimal pressure drop in the reaction tube.

DESCRIPTION OF THE PREFERRED EMBODIMENTS

The following specific examples further illustrate the present invention.

The reactor used in the examples consists of a 6,000 mm long reaction tube 26 mm in diameter and made of stainless steel. Such a reactor is illustrated in U.S. patent application Ser. No. 136,045. In each example, a first tube was filled with a catalyst further specified in the examples below. A second tube was filled with the same catalyst which previously was admixed with about 8% of its volume in Stuttgarter Masse containing promoter metal compounds.

The reactor tubes in all cases were surrounded by a sleeve containing water or water vapor to drain the heat of reaction. The supported catalysts always contained 19.5% by weight of silver. The support material used was an aluminum oxide support containing about 12% by weight of silicon dioxide. The first and second reaction tubes were operated simultaneously with the same gas mixture. This gas mixture had the following approximate composition:

| | |
|---|---|
| $C_2H_2$ | 25% by volume |
| $CH_4$ | 49% by volume |
| $O_2$ | 6.8% by volume |
| $CO_2$ | 4.5% by volume |
| $C_2H_6$ | 0.2% by volume |
| remainder Ar + $N_2$ | |

EXAMPLE 1

2.6 kg (2,500 ml) of the 19.5% by weight silver supported catalyst containing 507 g of silver were used in the first tube, containing no additional promoter as a control.

The second reaction tube, illustrating the invention, contained the same amount of this catalyst, which prior to being filled into the tube had been mixed with 200 ml of Stuttgarter Masse containing 1.1 g of potassium, 1.6 g of barium and 0.34 g of cesium which had been deposited in the form of an aqueous solution of barium peroxide, potassium carbonate and cesium nitrate.

In both cases, upon termination of the intake phase, the gas load was 9.25 (stp) $m^3$/l of catalyst at 19.8 bars gauge pressure, corresponding to a total gas load of 25 (stp) $m^3$/h. The chloride content in the circulating gas was kept at 7-8 mg of Cl/(stp) $m^3$ using 1,2-dichloroethane. The vapor chamber temperature was so controlled that an average concentration of 1.6% by volume of ethylene oxide was obtained at the reactor discharge.

| | start | | after 6 months' operation | |
|---|---|---|---|---|
| | selectivity mole % | temp. °C. | selectivity mole % | temp. °C. |
| 1st tube (control) | 74.0 | 254 | 71.6 | 271 |
| 2nd tube (invention) | 74.2 | 252 | 77.1 | 245 |

EXAMPLE 2

Example 1 was repeated with the silver supported catalyst in the first tube having 472 ppm of barium. For the otherwise equal conditions, the following results were obtained:

| | start | | after 6 months' operation | |
|---|---|---|---|---|
| | selectivity mole % | temp. °C. | selectivity mole % | temp. °C. |
| 1st tube (control) | 75.7 | 249 | 73.5 | 267 |
| 2nd tube | | | | |

-continued

|  | start | | after 6 months' operation | |
|---|---|---|---|---|
|  | selectivity mole % | temp. °C. | selectivity mole % | temp. °C. |
| (invention) | 75.8 | 249 | 77.9 | 245 |

EXAMPLE 3

Example 1 was repeated with the silver supported catalyst in the first tube having 481 ppm of barium and 91 ppm of cesium. The following results were obtained for otherwise equal conditions:

|  | start | | after 6 months' operation | |
|---|---|---|---|---|
|  | selectivity mole % | temp. °C. | selectivity mole % | temp. °C. |
| 1st tube (control) | 80.4 | 245 | 77.5 | 265 |
| 2nd tube (invention) | 80.3 | 245 | 81.5 | 242 |

EXAMPLE 4

As in Example 1, a pure silver supported catalyst (without promoter) was used in the first tube as the control catalyst. According to the present invention, the support layer mixed in the second tube received 0.29 g of rubidium in lieu of cesium. The following results were obtained:

|  | start | | after 6 months' operation | |
|---|---|---|---|---|
|  | selectivity mole % | temp. °C. | selectivity mole % | temp. °C. |
| 1st tube (control) | 74.0 | 254 | 71.6 | 271 |
| 2nd tube (invention) | 74.2 | 252 | 74.9 | 251 |

We claim:

1. In a process for the preparation of a supported silver catalyst having a promoter metal compound for the production of ethylene oxide by the controlled, vapor phase, partial oxidation of ethylene with molecular oxygen in the presence of said supported silver catalyst having a promoter metal compound, the improvement comprising increasing the activity and extending the service life of said catalyst by preparing a physical mixture of particles consisting essentially of:
   (a) supported silver catalysts and promoter metal compounds;
   (b) supported silver catalysts and supported promoter metal compounds;
   (c) promoter metal compound treated supported silver catalysts and promoter metal compounds; or
   (d) promoter metal compound treated supported silver catalysts and supported promoter metal compounds; said supported silver catalysts, said promoter metal compounds and said supported promoter metal compounds having the same shape and particle size so that uniform mixing is obtained.

2. The process of claim 1, wherein said promoter metal compounds are selected from the group consisting of compounds of potassium, rubidium, cesium, barium or mixtures thereof.

3. The process of claim 2, wherein said promoter metal compounds and said supported promoter metal compounds have a proportion by volume in the total mixture of about 0.5 to 25%.

4. The process of claim 2, wherein said promoter metal compounds have a concentration in percent by weight based on the total weight of catalyst of: about 0.001–0.05 rubidium; about 0.01–0.20 potassium; about 0.001–0.5 cesium or about 0.01–0.25 barium.

5. The process of claim 1, wherein said supported silver catalysts have about 2 to 20% by weight of silver on said support.

6. The process of claim 1, wherein said promoter metal compounds are selected from the group consisting of barium oxide, barium peroxide, barium hydroxide, barium nitrite, barium nitrate, barium carbonate, barium acetate, barium oxalate, barium tartrate, barium naphthenate, barium stearate, barium dodecanate, barium chloride, rubidium oxide, rubidium peroxide, rubidium hydroxide, rubidium nitrite, rubidium nitrate, rubidium carbonate, rubidium acetate, rubidium oxalate, rubidium tartrate, rubidium stearate, rubidium dodecanate, rubidium chloride, cesium oxide, cesium peroxide, cesium hydroxide, cesium nitrite, cesium nitrate, cesium carbonate, cesium acetate, cesium oxalate, cesium tartrate, cesium stearate, cesium dodecanate and cesium chloride.

7. The process of claim 1, wherein said particle size is about 2 to 10 mm.

8. The process of claim 7, wherein said particle size is about 2 to 5 mm.

* * * * *